United States Patent [19]

Arcuri et al.

[11] Patent Number: 4,558,030

[45] Date of Patent: Dec. 10, 1985

[54] RUTHENIUM-RHENIUM CATALYST ON TITANIA SUPPORT FOR FISCHER-TROPSCH SYNTHESIS

[75] Inventors: Kym B. Arcuri; Charles H. Mauldin; Dave H. Shaw, all of Baton Rouge, La.

[73] Assignee: Exxon Research and Engineering Co., Florham Park, N.J.

[21] Appl. No.: 626,024

[22] Filed: Jun. 29, 1984

[51] Int. Cl.$^4$ .................... B01J 21/06; B01J 23/64
[52] U.S. Cl. ................... 502/325; 502/350; 518/715
[58] Field of Search .............. 502/300, 325, 350; 518/715

[56] References Cited

U.S. PATENT DOCUMENTS

| | | |
|---|---|---|
| 1,603,101 | 11/1981 | Thompson et al. |
| 3,784,675 | 1/1974 | Kobylinski et al. ............. 423/213.5 |
| 3,972,837 | 8/1976 | Acres et al. .................... 252/473 |
| 4,042,614 | 8/1977 | Vannice et al. ................. 260/449 |
| 4,088,671 | 5/1978 | Kobylinski ..................... 260/449 |
| 4,089,810 | 5/1978 | Diwell et al. ................... 252/462 |
| 4,104,478 | 8/1978 | Trivedi ......................... 502/325 X |
| 4,176,088 | 11/1979 | Antos ........................... 502/325 X |
| 4,199,522 | 4/1980 | Murchison et al. ............ 260/449 R |

FOREIGN PATENT DOCUMENTS 1603101  11/1981  United Kingdom .

OTHER PUBLICATIONS

Fischer-Tropsch Synthesis of Hydrocarbons Over Ruthenium Supported on Transition Metal Oxides; Kikuchi, Nomura, Matsumoto and Morita (Waseda University, Tokyo 160); Pan-Pacific Synfuels Conference, vol. I, Nov. 17-19, 1982 Tokyo, pp. 1-10.

Fischer-Tropsch Synthesis Over Titania-Supported Ruthenium Catalysts; Kikuchi, Matsumoto, Takahashi, Machino and Morita (Waseda University, 3-4-1 Okubo, Shinjuku, Tokyo, Japan); Printed in the Netherlands; Applied Catalysis, 10 (1984), pp. 251-260.

IS-T-1006; Hydrogenation of Carbon Monoxide Over Ruthenium-Rhenium on Alumina Catalysts; D. E. Whitmoyer (M.S. Thesis Submitted to Iowa State University); Prepared for the U.S. Department of Energy Under Contract No. W-7405-Eng-82; Jul. 1982.

Primary Examiner—W. J. Shine
Attorney, Agent, or Firm—Llewellyn A. Proctor

[57] ABSTRACT

A novel ruthenium catalyst, notably a ruthenium-titania catalyst, is disclosed to which is added sufficient rhenium to obtain, at corresponding process conditions, improved activity maintenance in the production of hydrocarbons via carbon monoxide-hydrogen synthesis reactions vis-a-vis a catalyst composition otherwise similar except that it does not contain rhenium. High quality middle distillate fuels, characterized generally as admixtures of linear paraffins and olefins, are formed in a process wherein a feed mixture of carbon monoxide and hydrogen are contacted at reaction conditions over such catalyst.

13 Claims, No Drawings

RUTHENIUM-RHENIUM CATALYST ON TITANIA SUPPORT FOR FISCHER-TROPSCH SYNTHESIS

BACKGROUND OF THE INVENTION

I. Field of the Invention

This invention relates to improvements in the Fischer-Tropsch process, and Fischer-Tropsch catalysts. In particular, it relates to improved ruthenium catalysts, and process for using such catalysts in Fischer-Tropsch synthesis to produce hydrocarbons.

II. The Prior Art

Fischer-Tropsch synthesis originated with Franz Fischer and Hans Tropsch in the early nineteen twenties with the recognition that an admixture of carbon monoxide and hydrogen passed over iron turnings at 100-150 atmospheres and about 750°-840° F., produced oxygenated compounds and a small amount of hydrocarbons. At 7 atmospheres, and later at 1 atmosphere, Fischer found that the distribution between oxygenated and hydrocarbon products could be reversed. Fischer-Tropsch synthesis for the synthesis of hydrocarbons from carbon monoxide and hydrogen is now well known in the technical and patent literature. The first commercial Fischer-Tropsch operation utilized a cobalt catalyst, though later more active iron catalysts were also commercialized. An important advance in Fischer-Tropsch catalysts occurred with the use of nickel-thoria on kieselguhr in the early thirties. This catalyst was followed within a year by the corresponding cobalt catalyst, 100 Co: 18 $ThO_2$: 100 kieselguhr, parts by weight, and over the next few years by catalysts constituted of 100 Co: 18 $ThO_2$: 200 kieselguhr and 100 Co: 5 $ThO_2$: 8 MgO: 200 kieselguhr, respectively. The Group VIII non-noble metals, iron, cobalt, and nickel have been widely used in Fischer-Tropsch reactions, and these metals have been promoted with various other metals, and supported in various ways on various substrates. Most commercial experience has been based on cobalt and iron catalysts.

The use of ruthenium as a catalyst for the production of high-melting hydrocarbon wax from carbon monoxide and hydrogen has been known since the late thirties or early forties. Ruthenium is known as one of the more active catalysts, and its selectivity for making methane in the production of hydrocarbons is relatively low. Moreover, it is recognized as having a low carbon dioxide selectivity. The ruthenium catalyst thus behaves somewhat more ideally than many other catalysts, e.g. iron catalysts, in that more of the hydrogen and carbon monoxide of a synthesis gas are converted to hydrocarbons and water in accordance with the idealized equation: $2H_2 + CO \rightarrow (CH_2)_x + H_2O$; with less of the synthesis gas being converted to carbon dioxide, as in the equation: $H_2 + 2CO \rightarrow (CH_2)_x + CO_2$. The low carbon dioxide selectivity makes use of a ruthenium catalyst for the production of hydrocarbons particularly advantageous for use in processing synthesis gas derived by the conventional technique of steam reforming light hydrocarbon gases, e.g. refinery gas and natural gas.

U.S. Pat. No. 4,199,522, which issued on Apr. 22, 1980, to Murchinson et al, discloses an improved Fischer-Tropsch process, and catalyst which, inter alia, (1) consists essentially of about 1-95 wt. % (preferably about 10-50 wt. %) of at least one material selected from the group consisting of the sulfide, oxide or metal of Mo, W, Re, Ru, Ni, Pd, Rh, Os, Ir and Pt; (2) about 0.05-50 wt. % (preferably about 1-10 wt. %) of at least one material selected from the group consisting of the hydroxide, oxide or salt of Li, Na, K, Rb, Cs, Mg, Ca, Sr, Ba and Th; and (3) optionally a support, e.g. carbon, silica, zirconia, zircon (a mixture of zirconia and silica), titanium dioxide or mixtures thereof. The selectivity of the catalyst to produce $C_2$-$C_4$ olefins, especially $C_3$-$C_4$ olefins, is drastically increased. With the exception of thorium, the "laundry list" of possible first component metals are identical to those exemplified by Murchinson et al as metals previously known to be useful in Fischer-Tropsch reactions to produce "a variety of compounds; both hydrocarbons and oxygenated compounds."

In U.S. Pat. No. 4,042,614 to Vannice et al which issued Aug. 16, 1977, there is disclosed a ruthenium catalyst, the ruthenium being dispersed on $TiO_2$, other titanium-containing oxides or mixtures of titanium oxides, which provides superior synthesis characteristics in the conversion of carbon monoxide and hydrogen to hydrocarbons, notably olefinic hydrocarbons, particularly $C_2$ to $C_{10}$ olefins. These catalysts, like other ruthenium catalysts, have low methane selectivity, high activity, and low carbon dioxide selectivity. A major disadvantage of this catalyst, one which hampers commercial development, is its low activity maintenance; activity maintenance being defined as the length of time during an operating run that the total carbon monoxide conversion can be kept high, suitably at 90 percent, or higher, and the methane selectivity kept low, suitably at 10 percent, or lower, while maintaining a constant, preferably high, gas hourly space velocity. Activity maintenance is, of course, profoundly important in the consideration of a catalyst for commercial use since, in practice, activity must be maintained by periodically offsetting the effects of deactivation by increasing the operating temperature, and additionally, if desired, by occasionally cutting off the feed to the process, and exposing or contacting the catalyst with hydrogen. The belief is that the hydrogen treatments help to minimize the deactivation rate thereby extending the catalyst life. The elevation of temperature, or application of both of these techniques, has not adequately extended the life of these catalysts. With each temperature increase, there is degradation in product selectivity. Methane selectivity increases and the total yield of liquid hydrocarbon product decreases. Eventually, product selectivity deteriorates to the point where the catalyst must be regenerated, or replaced.

III. Objects

It is, accordingly, the primary objective of the present invention to obviate this disadvantage of supported ruthenium catalysts, notably ruthenium-titania catalysts, by providing new and improved supported ruthenium catalysts, notably ruthenium-titania catalysts, which in Fischer-Tropsch synthesis, provides significantly better activity maintenance than other supported ruthenium catalysts, notably ruthenium-titania catalysts, at corresponding process conditions.

A particular object is to provide a new and improved ruthenium-titania catalyst, and process of using such catalyst in carbon monoxide-hydrogen synthesis reactions, to obtain superior activity maintenance as contrasted with other ruthenium-titania catalysts, but similar to other ruthenium-titania catalysts in that other desirable catalytic properties of such catalysts are not significantly altered.

A further object is to provide a process for the preparation of hydrocarbons, notably high quality middle distillate fuels characterized generally as admixtures of linear paraffins and olefins, from a feed mixture of carbon monoxide and hydrogen via the use of such catalysts.

IV. The Invention

These objects and others are achieved in accordance with the present invention which, in general, embodies:

(A) A particulate catalyst composition constituted of a catalytically active amount of ruthenium, to which is added sufficient rhenium to obtain, at corresponding process conditions, improved activity maintenance in the production of hydrocarbons via carbon monoxide-hydrogen synthesis reactions than a catalyst composition otherwise similar except that it does not contain rhenium. Suitably, rhenium is added to the ruthenium catalyst in amount sufficient to form a catalyst having a rhenium:ruthenium in weight ratio ranging from about 10:1 to about 1:10, preferably from about 2:1 to about 1:4. In terms of absolute concentrations, from about 0.01 percent to about 8 percent of rhenium, preferably from about 0.1 percent to about 4 percent of rhenium, based on the total weight of the catalyst composition (dry basis), is dispersed with the required amount of ruthenium upon an inorganic oxide support, preferably upon titania, $TiO_2$, or a titania-containing support. Suitably, in terms of absolute concentrations the ruthenium is present in the composition in amounts ranging from about 0.01 percent to about 8 percent, preferably from about 0.2 percent to about 4 percent, based on the total weight of the catalyst composition (dry basis), and sufficient rhenium is added to form a catalyst having a rhenium:ruthenium ratio ranging from about 10:1 to about 1:10, preferably from about 2:1 to about 1:4, based on the total weight of the ruthenium and rhenium contained in the catalyst composition (dry basis). The absolute concentration of each metal is, of course, preselected to provide the desired ratio of rhenium:ruthenium, as heretofore expressed. These catalyst compositions, it has been found, produce a product which is predominately $C_{10}+$ linear paraffins and olefins, with very little oxygenates. They provide significantly better activity maintenance in the conversion of the carbon monoxide and hydrogen to hydrocarbons, at similar conditions, than catalysts otherwise similar except that they are not promoted with rhenium. The product selectivities and carbon monoxide conversion rates for the rhenium-promoted ruthenium catalyst and the unpromoted ruthenium catalyst are not significantly different. However, the activity maintenance of the ruthenium catalyst is considerably improved by promotion of the catalyst with rhenium, without significant alteration of the product selectivities and carbon monoxide conversion rates, or other desirable properties of the unpromoted ruthenium catalyst.

(B) A process wherein the particulate catalyst composition of (A), supra, is formed into a bed, and the bed of catalyst contacted at reaction conditions with a feed comprised of an admixture of carbon monoxide and hydrogen, or compound decomposable in situ within the bed to generate carbon monoxide and hydrogen, to produce a product of middle distillate fuel quality constituted predominately of linear paraffins and olefins. In general, the reaction is carried out at an $H_2:CO$ mole ratio ranging from about 0.1:1 to about 10:1, preferably from about 0.5:1 to about 4:1, at gas hourly space velocities ranging from about 100 $hr^{-1}$ to about 5,000 $hr^{-1}$, preferably from about 300 $hr^{-1}$ to about 2000 $hr^{-1}$, at temperatures ranging from about 150° C. to about 500° C., preferably from about 180° C. to about 300° C., and pressures ranging from about 100 $kP_a$ to about $10^5 kP_a$, preferably from about 100 $kP_a$ to about 3100 $kP_a$. In its most preferred form, a bed of catalyst comprised of from about 0.2 percent to about 4 percent ruthenium, containing sufficient rhenium to provide a catalyst containing rhenium:ruthenium in ratio ranging from about 2:1 to about 1:4, is dispersed on titania, preferably a high purity titania, and a bed of such catalyst is contacted with a gaseous admixture of carbon monoxide and hydrogen, or compound decomposable in situ within the bed to generate carbon monoxide and hydrogen. The synthesis reaction is carried out at an $H_2:CO$ mole ratio ranging from about 0.1:1 to about 10:1, preferably from about 0.5:1 to about 4:1, at space velocities ranging from about 100 $hr^{-1}$ to about 5,000 $hr^{-1}$, preferably from about 300 $hr^{-1}$ to about 2000 $hr^{-1}$, at temperatures ranging from about 150° C. to about 500° C., preferably from about 180° C. to about 300° C. and pressures ranging from about 100 $kP_a$ to about $10^5$ $kP_a$, preferably from about 100 $kP_a$ to about 3100 $kP_a$. The product generally and preferably contains 60 percent, more preferably 75 percent or greater, $C_{10}+$ liquid hydrocarbons which boil above 160° C. (320° F.).

It is found that ruthenium and rhenium supported on titania, or other titania-containing oxides provides a catalyst system which exhibits superior hydrocarbon synthesis characteristics in Fischer-Tropsch reactions. The titania-containing oxide supports used in the practice of this invention are preferably oxides having surface areas of from about 2 to about 150 $m^2g^{-1}$, preferably from about 10 to about 50 $m^2g^{-1}$. The dispersed rhenium and ruthenium possess a crystallite size, as determined by transmission electron microscopy of from about 1 to about 10 nm, preferably from about 1 to about 5 nm.

A preferred titania support is one having a weight ratio rutile:anatase of at least about 2:3, and more preferably at least about 3:2; the rutile:anatase ratio being determined by ASTM D 3720-78: Standard Test Method for *Ratio of Anatase to Rutile In Titanium Dioxide Pigments by Use of X-Ray Diffraction*. The titania can be used per se as a support, or in combination with other materials for forming a support. Suitably, the titania is one having a rutile:anatase ratio ranging from about 2:3 to about 100:1, more suitably from about 3:2 to about 100:1, and greater. This concentration of rutile provide generally optimum activity, and $C_{10}+$ hydrocarbon selectivity without significant cant gas and $CO_2$ make.

Rhenium-ruthenium/titania catalysts exhibit high selectivity in the synthesis of hydrocarbon liquids from carbon monoxide and hydrogen. The catalysts employed in the practice of this invention are prepared by techniques known in the art for the preparation of other catalysts. The catalyst can, e.g., be prepared by gellation, or cogellation techniques. Suitably however, a metal, or metals, can be deposited on a previously pilled, pelleted, beaded, extruded, or sieved support material by the impregnation method. In preparing catalysts, the metals are deposited from solution on the support in preselected amounts to provide the desired absolute amounts, and weight ratio of each respective metal. Suitably one metal can be first composited with the support, and then the other; or both may be added simultaneously. The amount of impregnation solution used should be sufficient to completely immerse the carrier, usually within the range from about 1 to 20 times of the carrier by volume, depending on the metal, or metals, concentration in the impregnation solution. The impregnation treatment can be carried out under a wide range of conditions including ambient or elevated temperatures. Metal components other than rhenium and ruthenium can also be added. The introduction of an additional metal, or metals, into the catalyst can be carried out by any method and at any time of the catalyst preparation, for example, prior to, following or simultaneously with the impregnation of the support with the ruthenium and rhenium components. In the usual operation, the additional component is introduced simultaneously with the incorporation of the ruthenium and rhenium components.

The catalyst, after impregnation, is dried by heating at a temperature above about 25° C., preferably between about 65° C. and 150° C., in the presence of nitrogen or oxygen, or both, in an air stream or under vacuum. The metals contained on the catalyst can then be reduced. Reduction is performed by contact of the catalyst with hydrogen or a hydrogen containing gas stream at temperatures ranging from about 150° C. to about 565° C. for periods ranging from about 0.5 to about 24 hours at from about 100 $kP_a$ to about 4000 $kP_a$. A gas containing hydrogen and inert components, or a gas containing hydrogen and carbon monoxide in admixture are satisfactory for use in carrying out the reduction.

The invention will be more fully understood by references to the following demonstrations and examples which present comparative data illustrating its more salient features. All parts are given in terms of weight except as otherwise specified.

In the examples, titania (Degussa P-25 $TiO_2$) was used as the support for all of the catalysts after mixing with sterotex, and after pilling, grinding, and screening to 60-150 mesh (Tyler). Three versions of $TiO_2$ were prepared by calcining portions of the $TiO_2$ in air at 500° C. and 600° C., respectively, overnight. This gave $TiO_2$ supports with the following properties:

| Temperature, °C. | % Rutile:Anatase Ratio | Surface Area $m^2/g$ | Pore Volume ml/g |
|---|---|---|---|
| 500 | 1.2:1 | 33-36 | 0.28-0.40 |
| 500[(1)] | 2:1 | 22-26 | 0.23-0.25 |
| 6000 | >30:1 | 10-16 | 0.11-0.15 |

[(1)]With subsequent reduction in hydrogen at 450° C.

Catalysts, of 60-150 mesh size, were prepared from selected portions of these materials by simple impregnation of the support with ruthenium nitrate (Engelhard) or perrhenic acid, or both, from acetone solution using a rotary evaporator, drying in a vacuum oven at 150° C. The catalysts were charged to a reactor, reduced in $H_2$ at 450° C. for 4 hours, and then reacted with syngas at the conditions described in the Examples.

Experimental runs have shown that the deactivation rate of the $Ru/TiO_2$ catalyst is essentially independent of small changes in process conditions, viz., pressure, and carbon monoxide conversion level. The example immediately following, however, shows that the activity maintenance of the $Ru/TiO_2$ catalyst can be significantly enhanced by the use of a rhenium promoted ruthenium catalyst, wherein the rhenium and ruthenium are dispersed on a corresponding $TiO_2$ support.

EXAMPLE 1

A synthesis gas comprised of an admixture of hydrogen and carbon monoxide in $H_2$:CO mole ratio of 2:1 was contacted (1), in a first run, with a rhenium promoted ruthenium/titania catalyst, Catalyst A (1% of Ru–0.5% Re/$TiO_2$), and (2) in another run, with an unpromoted ruthenium/titania catalyst (1% Ru/$TiO_2$), Catalyst B, at 230° C., 280 psig, and GHSV=1000. Both Catalysts A and B differed one from the other only in that Catalyst A was promoted with rhenium, and Catalyst B was not. The rhenium promoted catalyst, Catalyst A, was prepared in the same manner as the unpromoted catalyst, Catalyst B. In the preparation of the unpromoted catalyst the $TiO_2$ support which contained a rutile:anatase ratio of 2:1 was impregnated with an aqueous solution of $Ru(NO_3)_3$, and in the preparation of the promoted catalyst, the $TiO_2$ support was co-impregnated with perrhenic acid ($HReO_4$) and $Ru(NO_3)_3$ using, in both instances, a rotary-evaporator for solvent removal. After a period of 27 days each of these runs were terminated, and the deactivation rate determined by constructing a semi-log plot of a power law rate constant for CO conversion to hydrocarbons versus time. The slope of a regressed line drawn through the data represents a deactivation rate in terms of the change in rate constant ($\Delta \ln k$) per day. The power law rate constant is derived from the following equation:

$$k = \frac{-GHSV}{(23691)} \int_{(N_{CO})_{in}}^{(N_{CO})_{out}} \frac{(N_T)}{(N_{H2})^{1.5} (N_{CO})^{-0.5}} \frac{dN_{CO}}{P}$$

where:
$N_{CO}$ = moles of CO
$N_{H2}$ = moles of $H_2$
$N_T$ = moles of CO+$H_2$+products
P = reactor pressure
GHSV = gas hourly space velocity at 1 atm., 15.6° C.

Results are given in Table I.

TABLE I

| | 280 psig; 230° C., 1000 GHSV; $H_2$:CO = 2 | | | | | |
|---|---|---|---|---|---|---|
| | Deactivation Rate $\Delta \ln k$/day | Half-Life, Days | Steady State Mole % Selectivites | | Initial % CO Conversion | |
| | | | $CH_4$ | $CO_2$ | Total | To Hydrocarbons |
| Catalyst A (1% Ru— .5% Re)$TiO_2$ | −.003 ± .001 | 231 | 3.7 | 7.0 | 97 | 90 |
| Catalyst B (1% Ru/$TiO_2$) | −.0263 ± .016 | 26 | 3.5 | 1.5 | 97 | 94 |

These data thus show that the addition of Re to the $Ru/TiO_2$ catalyst leads to a significant reduction in the deactivation rate while maintaining low methane selectivity and comparable overall CO activity. Both catalysts, it is shown, exhibit similar hydrocarbon selectivities, but the rhenium promoted catalyst produces a slightly higher fraction of $CO_2$.

Quite clearly, therefore the rhenium promoted Ru/$TiO_2$ catalyst provides better activity maintenance at similar conditions. Product selectivities and CO conversion rates for the two catalysts are comparable.

The data presented in Example 2 show the effect of ruthenium and rhenium loadings in screening runs made of several rhenium promoted ruthenium-titania catalysts.

EXAMPLE 2

A series of runs were made at the conditions given in Example 1, with rhenium promoted ruthenium-$TiO_2$ catalysts having varying amounts of rhenium. The $TiO_2$ supports contain a rutile:anatase ratio of 1.2:1 as determined by x-ray diffraction. Reference is made to Table II:

TABLE II

| | | Conditions: 280 psig, 230° C., $H_2$:CO = 2, 1000 GHSV | | |
|---|---|---|---|---|
| Wt. % Ru | Wt. % Re | CO Conv. to Hydrocarbons | $CH_4$ Selectivity | $CO_2$ Selectivity |
| .1 | 1 | 11 | 4 | 20 |
| .5 | 0.5 | 33 | 7.5 | 5 |
| .75 | 0.5 | 43 | 9 | 6 |
| 1 | 0.5 | 82 | 5.6 | 6 |

These data clearly show that catalyst activity is proportional to the ruthenium loading, $CO_2$ selectivity increasing with increasing rhenium concentration. The data show that the most preferred Re/Ru ratio is in the range of about 2:1 to about 1:4. This composition is especially preferred in order to minimize $CO_2$ formation with >2:1 $H_2$/CO feeds such as those obtained from natural gas. If, on the other hand, the syngas were obtained from coal (<2:1 $H_2$/CO), the high shift activity present with Re/Ru ratios over 2:1 would provide an advantage in optimizing hydrocarbon yield.

The rutile content of the titania support also affects the rate of deactivation and selectivity, as demonstrated by the following example.

EXAMPLE 3

A series of catalysts (1% Ru-0.5% Re-$TiO_2$) were formed by impregnation of ruthenium and rhenium on $TiO_2$ supports having a rutile:anatase ratio of 1.2:1, 2:1 and >30:1, respectively, as described in Example 1. These catalysts were then contacted with a syn gas mixture, again as described by reference to FIG. 1, with the results given in Table III.

| Catalyst: | 1% Ru-0.5% Re—$TiO_2$ | | |
|---|---|---|---|
| Conditions: | 280 psig; 230° C.; $H_2$:CO = 2; GHSV; 90% CO Conversion | | |
| Rutile:anatase ratio, wt. | 1.2:1 | 2:1 | >30:1 |
| $CH_4$ Selectivity | 7 | 4.5 | 2 |
| Deactivation $\frac{(\Delta \ln k)}{day}$ | −.18 | −.003 | −.008 |
| Half Life, Days | 4 | 231 | 87 |
| Pore Volume, ml/gm | 0.4 | 0.2 | 0.15 |
| Surface Area, $m^2$/gm | 35 | 24 | 12 |

These data show clearly, particularly as relates to the rate of deactivation, and half life of the catalyst in days, that the high rutile content of the $TiO_2$ support suppresses $CH_4$ selectivity, and enhances catalyst activity maintenance. Titania catalysts having a rutile:anatase ratio greater than 2:3 are preferred.

It is apparent that various modifications and changes can be made without departing the spirit and scope of the present invention.

What is claimed is:

1. A catalyst composition useful for the synthesis of hydrocarbons from admixtures of carbon monoxide and hydrogen at reaction conditions which comprises: ruthenium in catalytically active amount composited with titania, or titania-containing support, having a rutile:anatase ratio of at least about 2:3 and rhenium in amount sufficient to provide a weight ratio of rhenium:ruthenium which ranges from about 2:1 to about 1:4, sufficient at corresponding reaction conditions to obtain improved activity maintenance vis-a-vis a ruthenium catalyst otherwise similar except that it does not contain rhenium.

2. The composition of claim 1 wherein the rutile:anatase ratio of the titania ranges from about 2:3 to about 100:1.

3. The composition of claim 1 wherein the catalyst contains from about 0.01 percent to about 8 percent ruthenium, based on the weight of the catalyst composition.

4. The composition of claim 1 wherein the catalyst contains from about 0.2 to about 4 percent ruthenium, based on the weight of the catalyst composition.

5. The composition of claim 1 wherein the catalyst contains from about 0.01 to about 8 percent rhenium, based on the weight of the catalyst composition.

6. The composition of claim 1 wherein the catalyst contains from about 0.1 to about 4 percent rhenium, based on the weight of the catalyst composition.

7. The composition of claim 1 wherein the rutile:anatase ratio of the titania ranges from about 3:2 to about 100:1, and greater.

8. The composition of claim 1 wherein the rutile:anatase ratio of the titania ranges from about 2:3 to about 100:1, and the catalyst contains from about 0.01 percent to about 8 percent ruthenium, based on the weight of the catalyst composition.

9. The composition of claim 8 wherein the catalyst contains from about 0.2 percent to about 4 percent ruthenium.

10. The composition of claim 1 wherein the rutile:anatase ratio of the titania ranges from about 2:3 to about 100:1, and the catalyst contains from about 0.01 percent to about 8 percent rhenium.

11. The composition of claim 10 wherein the catalyst contains from about 0.1 to about 4 percent rhenium.

12. The composition of claim 1 wherein the rutile:anatase ratio of the titania ranges from about 2:3 to about 100:1, the catalyst contains from about 0.01 percent to about 8 percent ruthenium, and from about 0.01 percent to about 8 percent rhenium, based on the weight of the catalyst composition.

13. The composition of claim 12 wherein the catalyst contains from about 0.2 to about 4 percent ruthenium, and from about 0.2 to about 4 percent rhenium.

* * * * *